(12) United States Patent
Oben

(10) Patent No.: US 10,279,001 B2
(45) Date of Patent: May 7, 2019

(54) METHODS AND COMPOSITIONS TO REDUCE FAT GAIN, PROMOTE WEIGHT LOSS IN MAMMALS

(71) Applicant: Julius Enyoug Oben, Cameroon (CM)

(72) Inventor: Julius Enyoug Oben, Cameroon (CM)

( * ) Notice: Subject to any disclaimer, the term of this patent is extended or adjusted under 35 U.S.C. 154(b) by 519 days.

(21) Appl. No.: 14/242,775

(22) Filed: Apr. 1, 2014

(65) Prior Publication Data

US 2014/0212521 A1    Jul. 31, 2014

Related U.S. Application Data

(62) Division of application No. 13/072,671, filed on Mar. 25, 2011, now Pat. No. 9,034,342.

(60) Provisional application No. 61/317,660, filed on Mar. 25, 2010.

(51) Int. Cl.
| | | |
|---|---|---|
| *A61K 36/185* | (2006.01) | |
| *A61K 36/48* | (2006.01) | |
| *A61K 36/888* | (2006.01) | |
| *A61K 31/015* | (2006.01) | |
| *A61K 35/748* | (2015.01) | |

(52) U.S. Cl.
CPC ............ *A61K 36/48* (2013.01); *A61K 31/015* (2013.01); *A61K 35/748* (2013.01); *A61K 36/185* (2013.01); *A61K 36/888* (2013.01)

(58) Field of Classification Search
None
See application file for complete search history.

(56) References Cited

U.S. PATENT DOCUMENTS

| | | | | |
|---|---|---|---|---|
| 3,148,114 | A * | 9/1964 | Fahrenbach | A61K 31/715 424/195.17 |
| 5,662,934 | A * | 9/1997 | Najarian | A61K 31/10 424/451 |
| 2006/0099324 | A1 * | 5/2006 | Aurio | A61K 31/715 426/656 |

FOREIGN PATENT DOCUMENTS

CN         1582999 A   *   2/2005

OTHER PUBLICATIONS

Furhman, J. "Pomegranate Power" from DiseaseProof: Eat Smart Live Healthy. Internet Date: Dec. 22, 2005 [Retrieved from the Internet on: Jun. 13, 2016]. Retrieved from: <URL: http://www.diseaseproof.com/archives/healthy-food-pomegranate-power-print.html>.*
Newman et al. "Pomegranate Seed Oil Rich in Cholesterol Blocking Sterols" from the chapter "Your Heart Will Love Pomegranates". From the book Pomegranate: The Most Medicinal Fruit. (pp. 65-66).*
Redlich et al. Atherosclerosis. vol. 145, Issue 2, Aug. 1999, pp. 425-432.*
Science News. "Blue-Green Algae Has Dual Cholesterol Lowering Abilities". Mar. 23, 1999 [Retrieved from the Internet on: Jun. 13, 2016]. Retrieved from: <URL: https://www.sciencedaily.com/releases/1999/03/990323050400.htm>.*
(U1) Kuate et al. Lipids in Health and Disease Published: 19 February 2010 9:20. 7 pages. (Year: 2010).*

* cited by examiner

*Primary Examiner* — Amy L Clark
(74) *Attorney, Agent, or Firm* — Steve Hassid; Partners Law Group, Inc.

(57) ABSTRACT

The present disclosure relates to compositions and related methods to reduce body weight, body fat, waist and hip size, plasma total cholesterol, LDL, triglycerides, blood glucose, leptin and C-reactive protein levels and increase in HDL and serotonin levels in a mammal. The LeptiCore® formulation disclosed, at both the low and high dosages, is helpful in the management of fat gain and its related complications. The higher dosage resulted in significantly greater reductions in body weight and triglyceride, blood glucose, and C-reactive protein levels, as well as increased serotonin levels.

2 Claims, 1 Drawing Sheet

Formulation of LEPTICORE

| Plant | Proper Name | Quantity per 300mg | Source Information |
|---|---|---|---|
| Loleptin™ (plant – polysaccharides and esterified fatty acids) | a blend of *Cyamopsis tetragonolobus* – Guar Gum *(30%)*, *Ceratonia siliqua* – Locust Bean Gum *(20%)* and *Amorphophallus konjac* – konjac *(50%)* | 246.75mg | *Cyamopsis tetragonolobus* (bean) *Ceratonia siliqua* (seed) *Amorphophallus konjac* (root) |
| Pomegranate extract | *Punica granatum* - Pomegranate | 6.9mg | *Punica granatum* (seed) |
| Beta-carotene | synthetic | 11.85mg | Synthetic |
| Phycocyanamines™ (Blue Green Algae high PEA blend) | *Aphanizomenon Flos Aquae* – blue green algae | 34.5mg | *Aphanizomenon Flos Aquae* (algae) |

METHODS AND COMPOSITIONS TO REDUCE FAT GAIN, PROMOTE WEIGHT LOSS IN MAMMALS

BACKGROUND

This application is a divisional of U.S. application Ser. No. 13/072,671, filed on Mar. 25, 2011 which claims priority to U.S. Application Ser. No. 61/317,660, filed on Mar. 25, 2010, both of which are incorporated herein by reference.

1. Field

This disclosure generally relates to compositions and methods that improve various health related factors and conditions. More specifically, the present disclosure relates to methods and compositions comprising LeptiCore®, which is a combination of various ingredients, to promote weight loss in obese and overweight human subjects and improve various health related parameters associated with obesity and metabolic syndrome. Additionally, the present disclosure also relates to compositions and related methods to reduce body weight, body fat, waist and hip size, plasma total cholesterol, LDL, triglycerides, blood glucose, leptin and C-reactive protein levels and increase in HDL and serotonin levels in a mammal.

2. General Background

Metabolic syndrome, a common disorder also known as Syndrome X and insulin resistance syndrome is (like many other obesity-related conditions) on the rise throughout the world. The American Heart Association criteria for metabolic syndrome include abdominal obesity, atherogenic dyslipidemia, elevated blood pressure, insulin resistance or glucose intolerance, prothrombotic state, and pro-inflammatory state.

As of 2001, some 47 million people in the United States had metabolic syndrome—which was projected to overtake cigarette smoking as the greatest risk factor of cardiovascular disease [1]. One of the accompanying conditions of metabolic syndrome that has not received as much attention is oxidative stress. This seems to be a key in the disease condition, and all efforts to address the independent components of metabolic syndrome should include an effort to reduce oxidative stress, which has not been clearly established to be a prelude or consequence of metabolic syndrome.

In an effort to delay the onset of heart disease and type-2 diabetes for the vast and ever-increasing numbers of overweight/obese persons now at high risk for these diseases, the current International Diabetes Foundation recommends pharmacological agents that specifically target individual components of metabolic syndrome [2-7]. Although these agents can have benefits, the combination of safety concerns, high costs, and the complex nature of the condition have encouraged the investigation of medicinal plants as natural supplements in its treatment.

LeptiCore® is a blend of plant-based polysaccharides, esterified fatty acids, pomegranate, polyphenols and ellagic acid, beta-carotene, and aphanizomenon flosaquae extract, which are components shown to reduce stored body fat, enhance weight loss, act as antioxidants and ameliorate the symptoms of metabolic syndrome. The exact formulation of LeptiCore® is shown in FIG. 1.

Research has shown that leptin serves as a regulator of body fat storage by modulating satiation, glycemic control and metabolism; and that reduction in serum leptin correlates with lower regional body fat and total body fat [8-10]. Leptin has also been shown to cause oxidative stress [11], which can further exacerbate metabolic syndrome.

Leptin is secreted by fat—the more fat, the more leptin—yet it is named for the Greek word leptos, which means "thin." While obese people produce much higher levels of leptin than thin and normal-weight individuals, they are somehow resistant to its effects [8, 12].

One reason for this may be that elevated levels of C-reactive protein (CRP), which inhibits leptin's role in controlling appetite [13]. CRP is now considered a key marker for low-grade systemic inflammation which, in turn, is considered by leading scientists to be responsible for a number of metabolic problems that result in unwanted weight gain and obesity [14]. Low grade, internal, invisible inflammation, oxidative stress, along with high leptin levels, may be a root cause of excess body fat and the inability to lose excess or unwanted fat [15].

In vivo and in vitro research done at the University of Pittsburgh demonstrated that CRP binds to leptin thereby impairing its signaling in two ways: 1) the coupling of CRP to leptin makes crossing the blood-brain barrier nearly impossible, thus preventing "free" leptin access to the hypothalamus; 2) the CRP/leptin complex inhibits the binding of leptin to its receptors, thus blocking its ability to signal in cultured cells. Since human CRP correlates with increased plasma leptin and adiposity, the results "suggest a potential mechanism to leptin resistance, by which circulating CRP binds to leptin and attenuates its physiological functions [16].

In one set of studies, the researchers delivered human leptin continuously for six days into mice which had receptors for leptin but lacked the ability to produce it. As expected, the plump mice ate less and lost weight, and their blood glucose levels normalized. Infusions containing both leptin and high doses of CRP, however, blocked the action of leptin. The plump mice just kept eating, getting fatter and fatter, and were no longer protected against diabetes. Giving CRP alone affected neither food intake nor body weight [16].

Another experiment showed that human liver cells increased CRP expression when exposed to leptin, which suggests that appetite may be regulated through a feedback loop that includes the liver in addition to the brain and leptin-secreting fat cells [16].

Of the various ingredients in the LeptiCore formulation, the plant-based polysaccharides and esterified fatty acids have been shown to lower leptin level, resulting in reduced appetite and weight loss [17, 18]. Various studies have shown that pomegranate extract contains polyphenolic compounds and beta-carotenes, which have considerable efficacy in lowering CRP, resulting in reduced inflammation and lowered cholesterol [19-21]. The reduction of inflammation and CRP promotes leptin's effectiveness, increasing the possibility of reduced appetite and weight loss. These components have also been shown to be effective antioxidants which will consequently improve the components of metabolic syndrome.

The last of the natural ingredients in this formulation, the phycocyanamines (blue green algae—a high phenylethylamine (PEA) blend) addresses the emotional aspects of metabolic syndrome by increasing the vital neurotransmitter, serotonin (5HT), a well known mood elevator [22,23]. Many studies have shown that serotonin affects eating behavior and body weight, and that increased serotonin plasma levels are associated with decreased food intake, reduced weight gain, and increased energy expenditure [24, 25].

The primary purpose of the present study was to determine the effects of two dosage levels of a unique, natural formulation containing the above agents on weight loss in patients with metabolic syndrome.

BRIEF DESCRIPTION OF THE DRAWINGS

FIG. 1 shows an exemplary formulation, as described and claimed in at least one embodiment.

SUMMARY

Methods

The study was an 8 week randomized, double blind, placebo-controlled design involving 92 obese (mean 8 MI>30 kg/m2) participants (37 males; 55 females; ages 1952; mean age=30.7). The participants were randomly divided into three groups: placebo (n=30), LeptiCore® formula A (IOW dose) (n=31) and LeptiCore® formula B (high dose) (n=31). Capsules containing the placebo or active formulations were administered twice daily before meals with 300 ml of water. None of the participants followed any specific diet nor took any weight-reducing medications for the duration of the study. A total of 12 anthropomorphic and serological measurements were taken at the beginning of the study and after 2, 4, 6, and 8 weeks of treatment.

Results

Compared to the placebo group, the two active groups showed statistically significant differences on all 12 variables by week 8. These included four anthropomorphic variables (body weight, body fat, waist and hip size) and eight measures of serological levels (plasma total cholesterol, LDL, HDL, triglycerides, blood glucose, serotonin, leptin, C-reactive protein). The two active groups also showed significant intra-group differences on all 12 variables between study onset and week 8.

DETAILED DESCRIPTION

Participants

Ninety-two obese participants were recruited for the 8-week study. Based on physical examination by a physician and laboratory screening tests, all participants met the American Heart Association criteria for metabolic syndrome, which include abdominal obesity, atherogenic dyslipidemia, elevated blood pressure, insulin resistance or glucose intolerance, prothrombotic state, and pro-inflammatory state.

Specific inclusion criteria included: BMI>30 kg/m2; total cholesterol>200 mg/dl; LDL cholesterol>160 mg/dl; HDL cholesterol<40 mg/dl; triglycerides>150 mg/dl; fasting blood glucose>100 mg/dl; and blood pressure>130/85 mmHg.

Specific exclusion criteria included: morbid obesity (BMI>40 kg/m2); diabetes mellitus requiring daily insulin management; pregnancy/lactation; active infection; and systemic disease such as HIV/AIDS, active hepatitis or clinical signs of active malignancy within the past 5 years. Other exclusion criteria included the use of any cholesterol-lowering medications 30 days prior to enrolling in the study and/or medication (e.g., steroids) that interfere with healing; and enrolment in another clinical study within the past 6 months.

Of the 92 subjects, 37 were male and 55 were female. The age range was 19-52 (mean age=30.7), and the mean BMI was >30 kg/m2.

The purpose, nature and potential risks of the study were explained to all patients and all gave a written informed consent before participation. The Cameroon National Ethics Committee approved the protocol. The study was conducted in accordance with the Helsinki Declaration (1983 version). None of the participants took any weight-reducing medication nor followed any specific diet during the duration of the study.

Study Design/Intervention

The study was a randomized, double blind, placebo-controlled design. Participants were randomly divided into three groups: placebo, LeptiCore® formula A (low dose) and LeptiCore® formula B (high dose). The placebo or active formulations were administered twice daily before meals with approximately 300 ml (8-10 oz.) of water. Formula A=1 capsule (300 mg each); Formula B=2 capsules (300 mg each). Since the active and placebo capsules were identical in shape, color, and appearance, neither the participants nor the researchers knew which capsule was administered.

All product formulations were supplied by Pipeline Nutraceuticals, Inc. Fairfield, Calif., USA. All encapsulating, bottling and packaging was supplied by and carried out by Protein Research, Inc., Livermore, Calif., USA.

During the study period, subjects were examined bi-weekly. Their body weight, percent body fat, and waist/hip circumferences were recorded, and serological analysis was performed. Subjective impressions (e.g., increased/decreased appetite, feelings of lightness, gastrointestinal pains, etc.) were solicited and recorded during each visit. The subjects were also asked about their physical activity and food intake although no major dietary changes or exercises were suggested.

Anthropometric Measurements

Body weight, body fat, waist and hip circumference were assessed at each visit with a Tanita™ BC-418 Segmental Body Composition Analyzer/Scale that uses bioelectrical impedance analysis for body composition analysis. Height was measured with a Harpended™ stadiometer, which measures the length of curved line staffage to the nearest 0.5 cm.

Participants (12-hour fasted) were encouraged to wear light clothing before measurements were taken. Waist and hip measures were obtained with a soft non-stretchable plastic tape. Waist circumference was measured on the narrowest and the widest parts of the trunk; hip circumference was obtained at the widest point of the hip. In an effort to ensure intra-individual consistency, the participants were measured at approximately the same time of day each visit.

Serological/Laboratory Methods

Blood samples were collected after a 12-hour overnight fast into heparinized tubes at the beginning of the study and after 2, 4, 6, and 8 weeks of treatment. The concentrations of total cholesterol, LDL cholesterol, HDL cholesterol, triglycerides, fasting blood glucose, serotonin, C-reactive protein, and leptin were measured using commercial diagnostic kits from SIGMA Diagnostics, St. Louis, Mo., USA.

Statistical Analysis

The data for each parameter were summarized (n, mean, standard deviation) for Week 0 (Initial) and Week 8 (final) and for the intra-group percent differences. The percent change from baseline was tested for differences using the Mixed Effects Model, a flexible tool for analyzing repeated and longitudinal treatments.

Results

Anthropomorphic characteristics (body weight, body fat, waist size, hip size)

As shown in Tables 1, 2, 3, and 4, over a period of 8 weeks the two treatment groups (Formula A=low dose; Formula B=high dose) showed a statistically significant decrease compared to the placebo group on all four variables. The only significant difference between the two formulations was in body weight loss (see Table 1).

Although the placebo group showed virtually no change (0.82 kg) in body weight over the 8-week trial, the Formula A group lost 5.2 kg ($p<0.001$), and the Formula B group lost 6.6 kg ($p<0.001$). In terms of intra-group mean-% change from baseline (Initial) to 8 weeks, the placebo, Formula A and Formula B groups lost 0.82%, 5.4% ($p<0.05$), and 6.95% ($p<0.001$), respectively.

TABLE 1

Body weight: effectiveness of treatments

| | Initial | Body Weight (mean kg) 8 Weeks | Weight Change (%) 8 Weeks − Initial |
|---|---|---|---|
| Formula B (↑ dose) | 100.93 ± 6.30 | 94.36 ± 5.67$^{b*}$ | −6.95$^{‡}$ |
| Formula A (↓ dose) | 102.28 ± 7.17 | 97.04 ± 5.95$^{b}$ | −5.40$^{†}$ |
| Placebo | 101.32 ± 6.13 | 100.50 ± 7.28 | −0.82 |

$^{a}p < 0.05$;
$^{b}p < 0.001$ compared with Placebo
$^{*}p < 0.05$;
$^{**}p < 0.001$ compared with Formula A
$^{†}p < 0.05$;
$^{‡}p < 0.001$ compared with Initial; intragroup analysis
Kuate et al. Lipids in Health and Disease 2010 9:20 doi: 10.1186/1476-511X-9-20

As with body weight, the placebo group showed little (0.1%) change in mean %-body fat after 8 weeks whereas the Formula A group lost 1.1% ($p<0.05$), and the Formula B group lost 1.8% ($p<0.05$). In terms of intra-group mean % change from baseline to 8 weeks, the placebo, Formula A and Formula B groups lost 0.24%, 2.8% ($p<0.05$), and 4.1% ($p<0.001$), respectively.

TABLE 2

Body fat: effectiveness of treatments

| | Initial | Body Fat (mean %) 8 Weeks | Fat Reduction (%) 8 Weeks − Initial |
|---|---|---|---|
| Formula B (↑ dose) | 43.85 ± 5.60 | 42.04 ± 6.63$^{a}$ | −4.13$^{‡}$ |
| Formula A (↓ dose) | 40.22 ± 7.26 | 39.08 ± 6.12$^{a}$ | −2.83$^{†}$ |
| Placebo | 42.28 ± 8.27 | 42.18 ± 8.117 | −0.24 |

$^{a}p < 0.05$;
$^{b}p < 0.001$ compared with Placebo
$^{*}p < 0.05$;
$^{**}p < 0.001$ compared with Formula A
$^{†}p < 0.05$;
$^{‡}p < 0.001$ compared with Initial; intragroup analysis
Kuate et al. Lipids in Health and Disease 2010 9:20 doi: 10.1186/1476-511X-9-20

Waist circumference is one of the most important determinants in the diagnosis of obesity and metabolic syndrome.

In this case, the Formula A and Formula B groups showed a 4.6 cm and 5.6 cm decrease, respectively, vs. the 0.6 cm decrease demonstrated by the placebo group (p<0.05). In terms of intra-group mean % change in waist size from baseline to 8 weeks, the placebo, Formula A and Formula B groups lost 0.57%, 4.4% (p<0.05), and 4.6% (p<0.001), respectively.

TABLE 3

Waist size: effectiveness of treatments

| | Initial | Waist Circumference (mean cm) 8 Weeks | Waist Change (%) 8 Weeks – Initial |
|---|---|---|---|
| Formula B (↑ dose) | 110.50 ± 7.28 | 105.38 ± 10.64$^a$ | −4.64$^‡$ |
| Formula A (↓ dose) | 104.00 ± 8.63 | 99.40 ± 11.73$^a$ | −4.42$^†$ |
| Placebo | 105.60 ± 7.91 | 105.00 ± 15.77 | −0.57 |

$^a$ p < 0.05;
$^b$ p < 0.001 compared with Placebo
*p < 0.05;
**p < 0.001 compared with Formula A
$^†$ p < 0.05;
$^‡$ p < 0.001 compared with Initial; intragroup analysis
Kuate et al. Lipids in Health and Disease 2010 9:20 doi: 10.1186/1476-511X-9-20

Once again, although the placebo group showed virtually no change (0.4 cm), the Formula A group lost 4.4 cm (p<0.05), and the Formula B group lost 5.6 cm (p<0.05) in circumference over the 8-week trial. In terms of intra-group mean % change from baseline to 8 weeks, the placebo, Formula A and Formula B groups lost 0.32%, 3.5% (p<0.05), and 4.6% (p<0.001), respectively.

TABLE 4

Hip size: effectiveness of treatments

| | Initial | Hip circumference (mean cm) 8 Weeks | Hip change (%) 8 Weeks – Initial |
|---|---|---|---|
| Formula B (↑ dose) | 123.38 ± 10.84 | 117.75 ± 17.24$^a$ | −4.56$^‡$ |
| Formula A (↓ dose) | 126.20 ± 12.91 | 121.80 ± 15.41$^a$ | −3.49$^†$ |
| Placebo | 125.85 ± 14.72 | 125.45 ± 17.99 | −0.32 |

$^a$ p < 0.05;
$^b$ p < 0.001 compared with Placebo
*p < 0.05;
**p < 0.001 compared with Formula A
$^†$ p < 0.05;
$^‡$ p < 0.001 compared with Initial; intragroup analysis
Kuate et al. Lipids in Health and Disease 2010 9:20 doi: 10.1186/1476-511X-9-20

Serological characteristics (total cholesterol, LDL cholesterol, HDL cholesterol, triglycerides, fasting blood glucose, serotonin, leptin, C-reactive protein)

As shown in Tables 5, 6, 7, 8, 9 and 10, the two treatments (vs. placebo) groups showed a statistically significant difference on all eight variables by the end of the 8-week trial period. There were significant differences between the two formulations (in favor of the high dosage Formula B) on triglyceride, blood glucose, serotonin, and C-reactive protein levels.

In contrast to the small (4.5 mg/dL) reduction in total cholesterol shown by the placebo group at 8 weeks, the reduction for the Formula A group was 37.6 mg/dL (p<0.05), and that of the Formula B group was 57.9 mg/dL (p<0.001). In terms of intra-group mean % change from baseline (Initial) to 8 weeks, the placebo group decrease was 2.1% whereas the Formula A and Formula B groups decreases were 18.0% (p<0.05) and 27.5 (p<0.001), respectively.

As with total cholesterol level, the placebo group showed a small (3.6 mg/dL) decrease in LDL cholesterol by 8 weeks. This can be compared with the 24.0 mg/dL reduction shown by the Formula A group (p<0.05) and the 32.8 mg/dL reduction of the Formula B group (p<0.001). In terms of intra-group mean % change in LDL from baseline to 8 weeks, the placebo, Formula A and Formula B groups decreased by 2.4%, 14.7% (p<0.05), and 19.8% (p<0.001), respectively.

On one of the few variables where an increase in level is desirable, the placebo group showed a very small (1.3 mg/dL) increase in HDL cholesterol at 8 weeks. This can be compared with the 4.7 mg/dL increase shown by the Formula A group (p<0.05) and the 6.2 mg/dL increase of the Formula B group (p<0.001). In terms of intra-group mean % change in HDL from baseline to 8 weeks, the placebo, Formula A and Formula B groups increased by 3.6%, 13.6% (p<0.05), and 19.1% (p<0.001), respectively.

TABLE 5

Plasma Total Cholesterol, LDL cholesterol and HDL cholesterol levels: effectiveness of treatments

| Variable | Group | Time (weeks) Initial | 8 | % Change 8 Weeks – Initial |
|---|---|---|---|---|
| Total Cholesterol (mg/dl) | Placebo | 211.16 ± 11.92 | 206.68 ± 20.19 | −2.12 |
| | Formula A (↓dose) | 208.74 ± 10.49 | 171.17 ± 18.82$^a$ | −18.00$^†$ |
| | Formula B (↑dose) | 210.64 ± 9.30 | 152.75 ± 10.19$^b$ | −27.48$^‡$ |
| LDL Cholesterol (mg/dl) | Placebo | 166.21 ± 9.25 | 162.63 ± 17.83 | −2.39 |
| | Formula A (↓dose) | 163.94 ± 8.27 | 139.91 ± 8.92$^a$ | −14.66$^†$ |
| | Formula B (↑dose) | 165.84 ± 7.29 | 133.05 ± 7.71$^b$ | −19.77$^‡$ |

TABLE 5-continued

Plasma Total Cholesterol, LDL cholesterol and HDL cholesterol levels: effectiveness of treatments

| Variable | Group | Time (weeks) Initial | 8 | % Change 8 Weeks − Initial |
|---|---|---|---|---|
| HDL Cholesterol (mg/dl) | Placebo | 35.92 ± 5.16 | 37.22 ± 5.59 | +3.62 |
| | Formula A (↓dose) | 34.72 ± 3.28 | 39.46 ± 4.48$^a$ | +13.65$^†$ |
| | Formula B (↑dose) | 32.43 ± 2.10 | 38.63 ± 3.11$^b$ | +19.12$^‡$ |

$^a$ p < 0.05;
$^b$ p < 0.001 compared with Placebo
*p < 0.05;
**p < 0.001 compared with Formula A
$^†$p < 0.05;
$^‡$p < 0.001 compared with Initial; intragroup analysis
Kuate et al. Lipids in Health and Disease 2010 9:20 doi: 10.1186/1476-511X-9-20

Per the above, the placebo group demonstrated a small change (1.0 mg/dL decrease) in triglyceride level at the end of the 8-week trial. This can be compared with the 11.5 mg/dL decrease shown by the Formula A group (p<0.05) and the 27.6 mg/dL reduction demonstrated by the Formula B group (p<0.001). In terms of intra-group mean % change in triglyceride level from baseline to 8 weeks, the placebo, Formula A and Formula B groups decreased by 0.6%, 7.1% (p<0.05), and 16.4% (p<0.001), respectively.

TABLE 6

Plasma Triglyceride level: effectiveness of treatments

| | Triglyceride (mean mg/dl) Initial | 8 Weeks | change (%) 8 Weeks − Initial |
|---|---|---|---|
| Formula B (↑ dose) | 167.61 ± 10.84 | 140.04 ± 4.29$^{b*}$ | −16.45$^‡$ |
| Formula A (↓ dose) | 162.21 ± 12.95 | 150.71 ± 8.30$^a$ | −7.09$^†$ |
| Placebo | 168.93 ± 14.04 | 167.90 ± 10.30 | −0.61 |

$^a$ p < 0.05;
$^b$ p < 0.001 compared with Placebo
*p < 0.05;
**p < 0.001 compared with Formula A
$^†$p < 0.05;
$^‡$p < 0.001 compared with Initial; intragroup analysis
Kuate et al. Lipids in Health and Disease 2010 9:20 doi: 10.1186/1476-511X-9-20

In contrast to the small (1.6 mg/dL) decrease in blood glucose level shown by the placebo group at 8 weeks, the reduction for the Formula A group was 8.4 mg/dL (p<0.05) and that of the Formula B group was 12.8 mg/dL (p<0.001). In terms of intra-group mean % change from baseline to 8 weeks, the placebo, Formula A and Formula B groups decreased by 1.5%, 7.9% (p<0.05), and 12.9% (p<0.001), respectively.

TABLE 7

Fasting Blood Glucose levels: effectiveness of treatments

| | Blood Glucose (mean mg/dl) Initial | 8 Weeks | change (%) 8 Weeks − Initial |
|---|---|---|---|
| Formula B (↑ dose) | 104.84 ± 9.39 | 92.06 ± 6.29$^{b*}$ | −12.19$^‡$ |
| Formula A (↓ dose) | 105.61 ± 8.62 | 97.22 ± 7.81$^a$ | −7.94$^†$ |
| Placebo | 107.52 ± 8.73 | 105.90 ± 10.79 | −1.51 |

$^a$ p < 0.05;
$^b$ p < 0.001 compared with Placebo
*p < 0.05;
**p < 0.001 compared with Formula A
$^†$p < 0.05;
$^‡$p < 0.001 compared with Initial; intragroup analysis
Kuate et al. Lipids in Health and Disease 2010 9:20 doi: 10.1186/1476-511X-9-20

In another case (see HDL cholesterol above) where an increase in level is desirable, the placebo group showed a very small (1.6 mg/dL) increase in serotonin levels at 8 weeks. This can be compared with the 9.9 mg/dL increase shown by the Formula A group (p<0.05) and the 13.7 mg/dL increase of the Formula B group (p<0.001). In terms of intra-group mean % change in serotonin from baseline to 8 weeks, the placebo, Formula A and Formula B groups increased by 9.1%, 28.6% (p<0.001), and 38.6% (p<0.001), respectively.

TABLE 8

Serum Serotonin levels: effectiveness of treatments

| | Serotonin (mean mg/dl) Initial | 8 Weeks | change (%) 8 Weeks − Initial |
|---|---|---|---|
| Formula B (↑ dose) | 35.40 ± 2.62 | 49.06 ± 2.85$^{b*}$ | 38.59$^‡$ |
| Formula A (↓ dose) | 34.55 ± 2.85 | 44.42 ± 2.96$^a$ | 28.57$^‡$ |
| Placebo | 34.20 ± 3.15 | 37.31 ± 3.69 | 9.09 |

$^a$ p < 0.05;
$^b$ p < 0.001 compared with Placebo
*p < 0.05;
**p < 0.001 compared with Formula A
$^†$p < 0.05;
$^‡$p < 0.001 compared with Initial; intragroup analysis
Kuate et al. Lipids in Health and Disease 2010 9:20 doi: 10.1186/1476-511X-9-20

In contrast to the 4.4 mg/dL decrease in serum leptin levels shown by the placebo group at 8 weeks, the reduction for the Formula A group was 14.8 mg/dL (p<0.05) and that of the Formula B group was 14.38 mg/dL (p<0.001). In terms of intra-group mean % change from baseline to 8 weeks, the placebo, Formula A and Formula B groups decreased by 14.4%, 47.0% (p<0.001), and 48.0% (p<0.001), respectively.

TABLE 9

Serum Leptin levels: effectiveness of treatments

|  | Initial | Leptin (mean mg/dl) 8 Weeks | change (%) 8 Weeks – Initial |
|---|---|---|---|
| Formula B (↑ dose) | 30.15 ± 1.50 | 15.83 ± 1.13$^b$ | −47.59$^‡$ |
| Formula A (↓ dose) | 31.52 ± 1.21 | 16.72 ± 1.40$^a$ | −46.95$^‡$ |
| Placebo | 30.33 ± 1.63 | 25.97 ± 1.61 | −14.38 |

$^a$p < 0.05;
$^b$p < 0.001 compared with Placebo
*p < 0.05;
**p < 0.001 compared with Formula A
$^†$p < 0.05;
$^‡$p < 0.001 compared with Initial; intragroup analysis
Kuate et al. Lipids in Health and Disease 2010 9:20 doi: 10.1186/1476-511X-9-20

Per the above, the placebo group demonstrated a small change (0.4 mg/l decrease) in C-reactive protein levels at the end of the 8-week trial. This can be compared with the 1.6 mg/l decrease shown by the Formula A group (p<0.05) and the 3.4 mg/l reduction demonstrated by the Formula B group (p<0.001). In terms of intra-group mean % change in blood levels of C-reactive protein from baseline to 8 weeks, the placebo, Formula A and Formula B groups decreased by 3.3%, 15.1% (p<0.001), and 29.4% (p<0.001), respectively.

TABLE 10

C-Reactive Protein levels: effectiveness of treatments

|  | Initial | CRP (mean mg/l) 8 Weeks | change (%) 8 Weeks – Initial |
|---|---|---|---|
| Formula B (↑ dose) | 11.58 ± 1.11 | 8.17 ± 0.61$^{b*}$ | −29.45$^‡$ |
| Formula A (↓ dose) | 10.99 ± 1.26 | 9.33 ± 0.43$^a$ | −15.10$^‡$ |
| Placebo | 12.46 ± 1.30 | 12.05 ± 1.39 | −3.31 |

$^a$p < 0.05;
$^b$p < 0.001 compared with Placebo
*p < 0.05;
**p < 0.001 compared with Formula A
$^†$p < 0.05;
$^‡$p < 0.001 compared with Initial; intragroup analysis
Kuate et al. Lipids in Health and Disease 2010 9:20 doi: 10.1186/1476-511X-9-20

Adverse Events

Adverse events with an incidence >3 included lack of sleep (4), and headache (4). Since the type and incidence of all reported side effects were also observed in the placebo group, one can assume that the LeptiCore® formulation had few, if any, negative side effects.

Discussion

The results herein indicate that the use of LeptiCore®, a unique natural formulation, has considerable efficacy on weight loss in patients with metabolic syndrome. Compared to the placebo group, the two active groups (low and high dosage) showed statistically significant differences on all 12 variables by the end of the 8-week trial. Although there were no differences between the two active groups on body fat, waist and hip size; or cholesterol (total, HDL, LDL) or leptin levels, the higher dosage did result in significantly greater reductions in body weight, and triglyceride, blood glucose, CRP and serotonin levels.

It appears that LeptiCore® somehow enhances cell membrane stability for improved cellular communication between the liver and adipose tissues for enhanced fatty acid utilization leading to regional fat loss. In addition, modulation of membrane-based inflammatory markers helped to reduce the inflammatory component of fat gain. This is where this formulation differs from other leptin-reducing supplements. Ingredients in this proprietary blend not only lowered serum leptin levels but also reduced CRP, a key marker for low-grade inflammation. As discussed earlier, some researchers believe the binding of CRP to leptin may be the reason [16]. The fact that CRP is elevated in obese people increases the plausibility of their argument. CRP, which is produced by the liver and typically rises as a part of the immune system's inflammatory response, has been gaining favor as a marker for hypertension and heart disease risk—both known complications of obesity.

LeptiCore's efficacy may also be due to the fact that it effects a time-dependent transit through the gastro-intestinal tract which, in turn, elicits a signal to regulate leptin levels. This is the mechanism for reducing the level of leptin in the bloodstream and the corresponding reduction in the percentage of body fat. LeptiCore's ability to lower CRP levels allows the remaining circulating leptin to reside in its "free" state and bind to appetite-regulating leptin receptors in the hypothalamus.

Yet another aspect of LeptiCore's action is its potential antioxidant power. The plasma concentrations of leptin are markedly increased in human obesity and positively correlated to body fat mass [26]. As human obesity is associated with hyperleptinemia and atherosclerosis, it was shown that leptin, in addition to its angiogenic properties, exerts proatherogenic effect on endothelial cells by increasing reactive oxygen species (ROS) formation. As mentioned earlier, Boulimie et al. [11] have shown that the administration of leptin may stimulate increases in oxidative stress in vitro cultured human endothelial cells. Increases in oxidative stress in the vascular endothelium may interact with nitric oxide to form peroxynitrite and thereby decrease the bioavailability of nitric oxide, which, in turn, could reduce weight gain and food intake [27].

Acknowledgements

The authors are grateful to Pipeline Nutraceuticals, Inc. Fairfield, Calif., USA and Protein Research, Inc., Livermore, Calif., USA for providing all the test material (Lepticore®) used in this study.

REFERENCES

[1] Ford ES, Giles WH, Dietz WH: Prevalence of the metabolic syndrome among US adults: findings from the third National Health and Examination Survey. JAMA 2002, 287:356-359.

[2] Knowler WC, Barrett-Connor E, Fowler SE, Hamman RF, Lachin JM, Walker EA, Nathan DM: Reduction in the incidence of type 2 diabetes with lifestyle intervention or metformin. N Engl J Med 2002, 346:393-403.

[3] Pyorala K, Ballantyne CM, Gumbiner B, Lee MW, Shah A, Davies MJ, Mitchel YB, Pedersen TR, Kjekshus J: Reduction of cardiovascular events by Simvastatin in non diabetic coronary heart disease patients with and without metabolic syndrome: Sub-group analyses of the Scandinavian Simvastatin Survival Study (4S). Diabetes Care 2004, 27:1735-1740.

[4] Buchanan TA, Xianag AH, Peters RK, Kjos SL, Marroquin A, Goico J, Ochoa C, Tan S, Berkowitz K, Hodis HN, Azen SP: Preservation of pancreatic p-cell function and prevention of type 2 diabetes by pharmacological treatment of insulin resistance in high risk Hispanic women. Diabetes 2002, 51:2796-2803.

[5] Chanoine JP, Hampl S, Jensen C, Boldrin M, Hauptman J: Effect of orlistat on weight and body composition in obese adolescents: a randomized controlled trial. JAMA 2002, 293:2932-2934.

[6] Lacey LA, Wolf A, O'Shea D, Erny S, Ruof J: Cost-effectiveness of orlistat for the treatment of overweight and obese patients in Ireland. Int J Obes 2005, 29:975-982.

[7] Swinburn BA, Carey D, Hills AP, Hooper M, Marks S, Proietto J, Strauss BJ, Sullivan D, Welborn TA, Caterson ID: Effect of orlistat on cardiovascular disease risk in obese adults. Diabetes Obes Metab 2005, 7:254-262.

[8] Klok MD, Jakobsdottir S, Drent ML: The role of leptin and ghrelin in the regulation of food intake and body weight in humans: a review. Obes Rev 2007, 8:21-34.

[9] Meier U, Gressner AM: Endocrine regulation of energy metabolism: review of pathobiochemical and clinical chemical aspects of leptin, ghrelin, adiponectin, and resistin. Clin Chem 2004, 50:1511-1525.

[10] Pelleymounter MA, Cullen MJ, Baker MB, Hecht R, Winters D, Boone T, Collins F: Effects of the obese gene product on body weight regulation in ob/ob mice. Science 1995, 269:540-543.

[11] Bouloumie A, Marumo T, Lafontan M, Busse R: Leptin induces oxidative stress in human endothelial cells. FASEB J 1999, 10:1231-1238.

[12] Reinehr T, Kratzsch J, Kiess W, Andler W: Circulating soluble leptin receptor, leptin, and insulin resistance before and after weight loss in obese children. Int J Obes (Lond) 2005, 29:1230-1235.

[13] Zamboni M, Di Francesco V, Garbin U, Fratta Passini A, Mazzali G, Stranieri C, Zoico E, Fantin F, Bosello O, Cominacini L: Adiponectin gene expression and adipocyte NF-kappaB transcriptional activity in elderly overweight and obese women: inter-relationships with fat distribution, hs-CRP, leptin and insulin resistance. Int J Obes (Lond) 2007, 31:1104-1109.

[14] Lavie CJ, Milani RV, Ventura HO: Untangling the heavy cardiovascular burden of obesity. Nat Clin Pract CardiovascMed 2008, 5:428-429.

[15] Mahadik SR, Deo SS, Mehtalia SD: Association of adiposity, inflammation and atherosclerosis: the role of adipocytokines and CRP in Asian Indian subjects. Metab Syndr Relat Disord 2008, 6:121-128.

[16] Chen K, Li F, Li J, Cai H, Strom S, Bisello A, Kelley DE, Friedman-Einat M, Skibinski GA, McCrory MA, Szalai AJ, Zhao AZ: Induction of leptin resistance through direct interaction of C-reactive protein with leptin. Nat Med 2006, 12:425-432.

[17] Weigle DS, Breen PA, Matthys CC, Callahan H S, Meeuws K E, Burden VR, Purnell JQ: A high-protein diet induces sustained reductions in appetite, ad libitum caloric intake, and body weight despite compensatory changes in diurnal plasma leptin and ghrelin concentrations. Am J Clin Nutr 2005, 82:41-8.

[18] Greco AV, Mingrone G, Favuzzi A, Capistro E, Gniuli D, Addolorato G, Brunoani A, Cavagnin F, Gasbarrini G: Serum leptin levels in post-hepatitis liver cirrhosis. J Hepatol 2000, 33:38-42.

[19] Huang TH, Peng G, Kota BP, Li GQ, Yamahara J, Roufogalis BD, Li Y: Pomegranate flower improves cardiac lipid metabolism in a diabetic rat model: role of lowering circulating lipids. BrJ Pharamcol 2005, 145:767-774.

[20] Heber D, Seeram NP, Wyatt H, Henning SM, Zhang Y, Ogden LG, Dreher M, Hill JO: Safety and antioxidant activity of a pomegranate ellagitannin-enriched polyphenol dietary supplement in overweight individuals with increased waist size. J Agric Food Chem 2007, 55:10050-10054.

[21] Devaraj S, Autret BC, Jialai I: Reduced-calorie orange juice beverage with plant sterols lowers C-reactive protein concentrations and improves the lipid profile in human volunteers. Am J ClinNutr 2006, 84:756-761.

[22] Sabelli H, Fink P, Fawcett J, Tom C: Sustained antidepressant effect of PEA replacement. J Neuropsychiatry Clin Neurosci 1996, 8:168-171.

[23] Sabelli HC, Javaid JI: Phenylethylamine modulation of affect: therapeutic and diagnostic implications. J Neuropsychiatry ClinNeurosci 1995, 7:6-14.

[24] Leombruni P, Piero A, Lavagnino L, Brustolin A, Campisis S, Fassino S: A randomized, double-blind trial comparing sertraline and fluoxetine 6-month treatment in obese patients with Binge Eating Disorder. Prog Neuropsychophamacol Biol Psychiatry 2008, 32:1599-1605.

[25] Arnold LM, McElroy SL, Hudson JI, Welge JA, Bennett AJ, Keck PE: A placebo-controlled, randomized trial of fluoxetine in the treatment of binge-eating disorder. J Clin Psychiatry 2002, 63:1028-1033.

[26] Caro JF, Sinha MK, Kolaczynski JW, Zhang PL, Considine RV: Leptin: the tale of an obesity gene. Diabetes 1996, 11:1455-1462.

[27] Morley JE, Flood JF: Effect of competitive antagonism of NO synthetase on weight and food intake in obese and diabetic mice. Am J Physiol 1994, 266(1 Pt 2): R164-168.

While the compositions and methods have been described in terms of what are presently considered to be the most practical and preferred embodiments, it is to be understood that the disclosure need not be limited to the disclosed embodiments. It is intended to cover various modifications and similar arrangements, the scope of which should be accorded the broadest interpretation so as to encompass all such modifications and similar compositions and methods.

The present disclosure provides method of reducing body weight, body fat, waist and hip size, plasma total cholesterol, LDL, triglycerides, blood glucose, leptin and/or C-reactive protein levels and increasing HDL and/or serotonin levels in an mammal, the method comprising providing a composition containing one or more ingredients selected from the group of: *Cyamopsis tetragonolobus*, Guar Gum, *Ceratonia siliqua*, Locust Bean Gum, *Amorphophallus konjac*, *Punica granatum*-Pomegranatekonjac, *Aphanizomenon Flos Aquae*, *Cyamopsis tetragonolobus* bean, *Ceratonia siliqua* seed, *Amorphophallus konjac* root, *Punica granatum* seed and *Aphanizomenon*.

The present disclosure also provides compositions containing one or more ingredients selected from the group of: *Cyamopsis tetragonolobus*, Guar Gum, *Ceratonia siliqua*, Locust Bean Gum, *Amorphophallus konjac*, *Punica granatum*-Pomegranatekonjac, *Aphanizomenon Flos Aquae*, *Cyamopsis tetragonolobus* bean, *Ceratonia siliqua* seed, *Amorphophallus konjac* root, *Punica granatum* seed and *Aphanizomenon* and their related methods to reduce body weight, body fat, waist and hip size, plasma total cholesterol, LDL, triglycerides, blood glucose, leptin and C-reactive protein levels and increase in HDL and serotonin levels in an mammal.

I claim:

1. A composition for reducing cholesterol, weight, triglycerides, blood glucose, inflammation, and leptin levels, and increasing HDL and serotonin levels, the composition comprising:
   a mixture of *Cyamopsis tetragonolobus*, *Ceratonia siliqua*, and *Amorphophallus konjac* in a ratio of 3:2:5, respectively, wherein the composition further comprises effective amounts of *Punica granatum* seed, Beta-carotene, and *Aphanizomenon flos aqua*, and wherein the composition is in the form of a capsule.

2. The composition of claim 1, wherein the beta-carotene is synthetic.

* * * * *